United States Patent [19]

Shau et al.

[11] Patent Number: 5,250,295
[45] Date of Patent: Oct. 5, 1993

[54] NATURAL KILLER CELL ENHANCING FACTOR

[75] Inventors: Hungyi Shau, Cerritos; Sidney H. Golub, Los Angeles, both of Calif.

[73] Assignee: The Regents of the Univ. of California, Oakland, Calif.

[21] Appl. No.: 787,148

[22] Filed: Nov. 4, 1991

[51] Int. Cl.$^5$ .................... A61K 37/02; C07K 15/06
[52] U.S. Cl. .................... 424/85.2; 424/85.1; 514/12; 514/21; 530/380; 530/402; 530/816; 530/829
[58] Field of Search .................... 424/85.1, 85.2, 85.4; 530/402, 410, 815, 816, 380, 829; 514/12, 21

[56] References Cited

U.S. PATENT DOCUMENTS 4,883,661  11/1989  Daly et al. ............... 517/2
5,208,218   5/1993  Van Snick et al. ........ 514/8

OTHER PUBLICATIONS

Shau, H. and Golub, S. "Modulation of Natural Killer-Mediated Lysis by Red Blood Cells", Cellular Immunology 116, 60-72, 1988.

Karger, S., "Abstract from Seventh International Workshop on Natural Killer Cells", Jun. 4-7, 1991, Stockholm, Sweden.

Iho, S., Shau, H. and Golub, S., "Characteristics of Interleukin-6-Enhanced Lymphokine-Activated Killer Cell Function", Cellular Immunology 135, 66-77 (1991).

Primary Examiner—Jeffrey E. Russel
Attorney, Agent, or Firm—Poms, Smith, Lande & Rose

[57] ABSTRACT

A factor (NKEF) for use in enhancing the activity of natural killer cells both in vivo and in vitro. NKEF is a soluble red blood cell cytosol protein having a molecular mass of between about 300 and 400 kilodaltons as determined by gel filtration high pressure liquid chromatography and an apparent molecular weight of about 48 kilodaltons as determined by non-reducing SDS-PAGE.

20 Claims, No Drawings

NATURAL KILLER CELL ENHANCING FACTOR

This invention was made with government support under Grant No. CA 3442 awarded by the National Institutes of Health. The government has certain rights in the invention.

BACKGROUND OF THE INVENTION

1. Field of the Invention

The present invention relates generally to methods and compositions which are effective in increasing or enhancing the cytotoxic effectiveness of human natural killer cells. More particularly, the present invention relates to the discovery and purification of a protein from red blood cell cytosol which is an effective factor that enhances the activity of natural killer cells.

2. Description of Related Art

The publications and other reference material referred to herein to describe the background and the detailed description of the invention and to provide additional detail regarding its practice are hereby incorporated by reference. For convenience, the referenced materials are numerically referenced and grouped in the appended bibliography.

Natural killer (NK) cells are a subset of lymphocytes found in blood and lymphoid tissues and especially the spleen. NK cells are derived from bone marrow and appear as large lymphocytes with prominent cytoplasmic granules. They are sometimes referred to as large granular lymphocytes. NK cells are believed to be responsible for natural surveillance against tumor growth and metastasis and are important regulators for hematopoiesis, including erythropoiesis (1-3).

The activity of NK cells has been shown to increase when several different protein products are present. These protein products include interferons, IL-1, IL-2, IL-6, several types of interferon and tumor necrosis factor-α (4-7). In addition, a B cell product termed NK stimulating factor (NKSF) (12) or cytotoxic lymphocyte maturation factor (13), has been reported as another activator of NK cells. All of these proteins have been purified, identified and cloned.

It has also been demonstrated that NK cells express higher cytotoxic activity against tumor cells in the presence of red blood cells (RBC) (8). Red blood cells are the major cellular component of the peripheral blood and occupy up to one-half of the total blood volume. Therefore, NK cells are usually in constant contact with RBC in the blood and, in fact, have a specific receptor, CD2, that facilitates interactions with RBC (9, 10).

The mechanism by which red blood cells enhance NK cell activity is not entirely known. For example, it has not been established whether the red blood cell itself is responsible for enhancing cytotoxicity or if one or more cellular products are responsible. Accordingly, there is a present need to establish the mechanism by which red blood cells enhance NK cell activity. Further, it would be desirable to isolate and identify any specific cellular components or cellular products which cause the observed NK cell enhancement. Such components or factors could then be used together with or apart from the red blood cell to enhance NK cell activity.

SUMMARY OF THE INVENTION

In accordance with the present invention, a protein which is present in red blood cells and which is capable of enhancing NK cell cytotoxicity has been isolated and identified. The protein or NK-enhancing factor (NKEF) has a molecular mass of between 300 and 400 kilodaltons and an apparent molecular weight of 48,000 daltons as measured by SDS-PAGE. NKEF is located in the cytosol of red blood cells. NKEF is water soluble and includes the peptide sequences set forth in SEQ.ID.NOS. 1, 2 and 3.

In accordance with the present invention, it was discovered that NKEF enhances the cytotoxic activity of NK cells provided that the NKEF is linked to an anchor moiety or support surface. Further, it was discovered that NKEF is effective in increasing NK cell activity when used alone or when used in combination with other NK cell enhancement proteins, such as Interleukin-2.

NKEF in accordance with the present invention is useful in both in vivo and in vitro applications where it is desirable to stimulate NK cell activity. As a feature of the present invention, the NKEF is linked to surfaces, such as the surface of a plastic test well, when the NKEF is used for in vitro testing. When used in vivo, the NKEF may or may not be linked to an anchor moiety which is adapted for introduction into the blood stream or other in vivo system.

As a feature of the present invention, NKEF has been found to not only be effective in enhancing NK cell activity, but to also be effective with IL-2 to induce lymphocyte activation and proliferation. Accordingly, NKEF may be used for combined immunotherapy with cytokines, such as IL-2, tumor necrosis factor, interferon and the like, to increase the function of B cells, T cells, macrophages, NK cells and other leukocytes.

As another feature of the present invention, it was discovered that NKEF is expressed by cells which are not of erythroid origin. Although isolation of NKEF from red blood cell cytosol is the preferred method of obtaining NKEF, other cell types, such as melanoma cells and B lymphoma cells have also been found to express NKEF.

The above discussed and many other features and attendant advantages of the present invention will become readily apparent as the invention is better understood by a reference to the following detailed description.

DETAILED DESCRIPTION OF THE INVENTION

The NK-enhancing factor (NKEF) in accordance with the present invention is a water soluble red blood cell protein which is located in the cell cytosol. NKEF has so far only been isolated from human red blood cell cytosol. However, NKEF may also be present in the cytosol of red blood cells present in other mammals. The following detailed description will be limited to the isolation, identification and use of NKEF present in human red blood cells with it being understood that NKEF isolated from other sources are contemplated by the present invention. For example, NKEF has been isolated from a melanoma cell line maintained at the University of California at Los Angeles (UCLA) and identified as UCLA-SO-M14. NKEF has also been isolated form a B lymphoma cell line which is also maintained at UCLA and identified as the Raji cell line.

NKEF has a molecular mass of between 300 and 400 kilodaltons as determined by gel filtration chromatography. The apparent molecular weight of NKEF, as determined by sodium dodecyl sulfate polyacrylamide gel electrophoresis (SDS-PAGE) under non-reducing conditions, is about 48 kilodaltons. Under reducing conditions, the apparent molecular weight by SDS-PAGE is about 24 kilodaltons. In regular aqueous solution, NKEF is believed to be a polymer. In the presence of SDS, NKEF appears as a dimer of subunits of the same molecular weights associated by disulfide bonds.

The amino acid sequence of NKEF has only been partially identified. The N-terminal of NKEF is believed to be blocked. However, partial amino acid sequences of NKEF have been obtained for three separate tryptic peptides. The peptide sequences are as follows:

Peptide (SEQ ID NO:1) 1:
    Gly—Leu—Phe—Ile—Ile—Asp—Tyr—Thr—Asp—Glu—Met—Gly—Glu—Val—Xaa—Pro—Ala—Gly—Gly—Lys Peptide (SEQ ID NO:2) 2:
    Leu—Val—Gln—Ala—Phe—Gln—Gly—Lys—Val—Asn—Val—Phe—Leu—Gln—Phe Peptide (SEQ ID NO:3) 3:
    Tyr—Leu—Val—Leu—Phe—Phe—Tyr—Pro—Leu—Asp—Phe—Thr—Phe—Val—Cys—Pro—Thr—Glu—Ile—Ile—Xaa—Cys—Pro—Thr—Glu—Ile—Ile—Gly The identification of the methionine and penultimate glycine amino acids in Peptide 1 are believed to be accurate. However, the presence of these two amino acids in Peptide 1 have not been positively identified. Similarly, the identification of the second leucine amino acid in Peptide 2 is also believed to be accurate, but has not been positively verified.

NKEF can be isolated from human red blood cell cytosol and purified using any of the well-known protein separation and purification processes. The initial preparation of the RBC's is preferably accomplished by known centrifugation techniques utilizing density gradients (8). Initial separation of the cytosol from the RBC can also be accomplished according to well known separation techniques. Preferably, the red blood cells are lysed by hypotonic shock with distilled and deionized water (ddH$_2$O). The resulting RBC cytosol and membrane fractions are then preferably separated by centrifugation. The resulting cytosol fraction is preferably suspended in ddH$_2$O prior to further treatment.

A preferred procedure for separating NKEF from the suspended cytosol fraction involves initial precipitation of the protein using ammonium sulfate. Ammonium sulfate is slowly added to the cytosol until the cytosol is 50% saturated with ammonium sulfate. NKEF begins to precipitate from the cytosol at 20% ammonium sulfate saturation. However, 50% saturation is preferred since it provides optimum NKEF recovery without precipitating hemoglobin. Hemoglobin begins to precipitate at ammonium sulfate saturation levels on the order of 60% and higher.

The relatively impure NKEF which is precipitated from the cytosol is preferably further purified using a combination of ion exchange chromatography, dialysis and high pressure liquid chromatography (HPLC). NKEF is easily identified by its molecular mass of 300 to 400 kilodaltons and its apparent molecular weights as determined by SDS-PAGE under non-reducing and reducing conditions.

Once the NKEF has been isolated based on molecular mass and apparent molecular weights, its identity can be further confirmed by comparing the amino acid sequences of tryptic peptides obtained from the NKEF to the amino acid sequences set forth above. Further, the ability of the isolated protein to enhance NK cell activity provides additional confirmation that the appropriate protein has been isolated.

NKEF is useful as a factor to enhance the activity (i.e.cytotoxicity) of NK cells both in vivo and in vitro. For in vitro applications, the NKEF is applied directly to the test well of the microtiter tray or other test tray. The effectiveness of NKEF in enhancing NK cell activity is increased substantially when the NKEF is linked or otherwise attached to the surface of the test well. Accordingly, it is preferred that the NKEF be added as an aqueous solution to the test well and allowed to bind to the test well surface for approximately one hour. The excess NKEF is then removed from the well prior to addition of the NK cells, target cells and other test ingredients. The preferred test well material is the plastic commonly used for test trays. Glass and other materials may also be used provided that they do not denature the NKEF. The in vitro uses for NKEF include cytotoxicity assays and other related tests directed to measuring and evaluating NK cell activity.

With respect to in vivo applications, it is believed that NKEF is an effective factor which will enhance the cytotoxic activity of the NK cells provided that the NKEF is linked to an appropriate anchor or carrier moiety before or after it is administered. Anchor moieties which may be linked to NKEF prior to administration include any of the common carrier molecules which are in use including both natural and synthetic polymers.

Exemplary anchor moieties include inert microparticulates, such as ceramics, plastic and glass. Organic anchor moieties include any of the proteins which can link with NKEF without denaturing it and which are capable of being transported with the NKEF through the blood stream or other fluid system in the body. Preferred protein anchor moieties are those which are related to or derived from the red blood cell membrane. Exemplary anchor moieties include polyethylene glycol and liposomes.

The NKEF may also be administered directly to the patient with linkage to a suitable anchor moiety taking place in vivo. When introducing non-anchored NKEF in vivo, it is preferred that the NKEF be protected from undesirable competitive protein binding. Such protection can be provided by encapsulating the NKEF in liposomes or other similar protective barrier.

The dosage ranges for the administration of NKEF are those large enough to produce the desired effect in which the cytotoxic activity of the NK cells show some degree of enhancement or increase. The dosage should not be so large as to cause adverse side effects. Generally, the dosage will vary with the age, condition, sex and extent of the disease in the animal and can be determined by one of skill in the art. The dosage can be adjusted by the individual physician in the event of any counterindications. Dosage can vary from less than 1 mg/kg/dose to about 100 mg/kg/dose, preferably about 5 mg/kg/dose to 10 mg/kg/dose, in one or more dose administrations daily.

NKEF in accordance with the present invention can be administered parenterally by single injections or by gradual infusion over time. NKEF can be administered intravenously, intraperitoneally, intramuscularly, subcutaneously, intracavitarily, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such a ethyl oleate. Aqueous carriers include water, alcoholic/aqueous solutions, emulsions or suspensions, including saline and buffered media. Parenteral vehicles include sodium chloride solution, Ringer's extrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

The above disclosure generally describes the present invention. A further understanding can be obtained by reference to the following specific examples which are provided for purposes of illustration and are not intended to be limiting.

ISOLATION AND PURIFICATION OF NKEF

Peripheral blood lymphocytes (PBL) and RBC from healthy donors were prepared by centrifugation over density gradients as previously described (6). PBL were resuspended in culture medium (CM) which was RPMI1640 supplemented with 10% heat-inactivated human AB serum, and were used as effector cells for NK cytotoxicity assay. To obtain subcellular components of RBC, RBC were lysed by hypotonic shock with 10 volumes of distilled deionized water ($ddH_2O$).

RBC cytosol and membrane fractions were then separated by centrifugation at $20,000 \times g$ for 15 minutes. The RBC membrane fraction was washed 3 times with $ddH_2O$, centrifuged and resuspended in one third of the volume of $ddH_2O$ that was used to suspend the cytosol.

The NKEF was initially separated from the cytosol by slowly adding ammonium sulfate to RBC cytosol. The precipitated molecules were dissolved with the original volume of phosphate buffered saline (PBS) and twice reprecipitated with same concentration of ammonium sulfate. The precipitated fractions and the soluble fractions were extensively dialyzed against buffer before testing NKEF activity. The NKEF was precipitated by as little as 20% saturated ammonium sulfate. In contrast, hemoglobin precipitated at above 60% saturated ammonium sulfate. Therefore, for optimal recovery of NKEF with minimal hemoglobin contamination, 50% saturated ammonium sulfate was chosen as the concentration for purification of NKEF.

The ammonium sulfate precipitated NKEF was further purified by ion exchange chromatography and tested for NKEF activity. The partially purified NKEF was dialyzed against 20 $\mu$M of tris-HCl buffer (pH 8.0) and applied to a Q-Sepharose column (LKB-Pharmacia) ($2 \times 30$ cm) preequilibrated with the same buffer. The column was eluted with 400 ml of a 0 to 2M NaCl gradient at 4 ml/2 min/fraction. The NaCl in eluted fractions was dialyzed out against tris-HCl buffer before testing for NKEF activity. The NaCl in the eluted fractions may be left in since it does not change NKEF activity in the Q-Sepharose separated fractions.

After Q-Sepharose separation, NKEF was further purified by HPLC with a TSK 250 gel filtration column. Ammonium sulfate and Q-Sepharose separated NKEF was applied to an Bio-Sil TSK-250 gel filtration column ($300 \times 7.5$ mm) (Bio-Rad, Richmond, Calif.) and eluted with 20 mM tris-HCl (pH 8.0) buffer at the rate of 1 ml/min/fraction. The major protein peak was detected between 7 and 8 minutes after sample injection. Both the protein peak and the NKEF activity peak were detected in fraction 8. The molecular mass of NKEF was estimated to be between 300 and 400 kilodaltons by comparing elution volumes with known molecular weight markers.

CHARACTERIZATION OF NKEF

To characterize NKEF and determine whether it is a protein, partially purified NKEF was incubated and treated with 12.5 mg/ml of porcine pancreas trypsin for 18 hr. at 37° C. and then tested for NKEF activity. Trypsin treated NKEF was then used to coat microwells to determine the effect on NK cytotoxicity. As controls, NKEF and trypsin were separately treated in similar conditions. Both RBC cytosol and NKEF partially purified by 50% saturated ammonium sulfate have been tested with similar results.

The treatment of NKEF with trypsin totally abolishes its activity demonstrating that a protein component is responsible for NKEF activity. Trypsin alone, after overnight incubation and dilution to the level in the assay medium, had no direct effect on NK activity.

NKEF purity and molecular weight estimates were measured by SDS-PAGE (11) with 12% slab gels. For reducing conditions, the samples were treated with 2.5% of 2-mercaptoethanol. For non-reducing conditions the samples were treated with 300 mM of N-ethylmalimide. The molecular weight of NKEF was estimated from prestained standards in parallel lanes (Bio-Rad, Richmond, Calif.). Under non-reducing conditions, NKEF appeared as a single band at 48,000 daltons position of the gels. In reducing gels, NKEF appeared as a 24,000 dalton band. SDS-PAGE of a reduced sample of NKEF exhibits a very faint band at 48,000 daltons as well, which is believed to be residual unreduced NKEF. The SDS-PAGE results show that NKEF is a dimer of subunits of same molecular weights associated by disulfide bonds. The HPLC results show that these dimers aggregate non-covalently to form polymers of between 300 kilodaltons and 400 kilodaltons mass in aqueous solution.

A specific serum against human NKEF was also generated. The 24,000 dalton band of SDS-PAGE purified NKEF was cut from the reduced gels, squeezed through a 18 gauge syringe needle, mixed with equal volumes of Freund's complete adjuvant and injected into rabbits. After several injections the rabbits were bled and the immune sera were tested for antibody against NKEF by Western blot analysis and ELISA. Results from ELISA show that immune but not preimmune rabbit serum reacts strongly with RBC cytosol.

Western blot analysis of the reduced gel indicates that the immune serum reacts with a 24,000 dalton component in human RBC cytosol. A faint band is sometimes detected at the 48,000 dalton position by Western Blot. The reactivity of the polyclonal antibody to the band at 48,000 daltons indicates that not all of the NKEF in the sample was reduced to its monomer.

In order to determine NKEF's amino acid sequences, tryptic peptides of NKEF were separated by reversed-phase HPLC with a C18 column (Waters, Rochester, Minn.). The column was eluted with a gradient of acetonitrile in 10 mM trifluoroacetic acid and the separated peptides were sequenced by automated Edman degradation on a Proton 1090E Sequencer. Due to unsuccessful attempts to determine the N-terminal sequence of NKEF, it is believed that the N-terminus of the protein is blocked. Tryptic peptides were prepared and separated by reverse-phase HPLC. Partial sequences were obtained from three of these peptides and are listed as follows (Xaa-represents an undetermined residue):

Peptide (SEQ ID NO:1) 1:
      Gly—Leu—Phe—Ile—Ile—Asp—Tyr—Thr—Asp—Glu—Met—Gly—Glu—Val—Xaa—Pro—Ala—Gly—Gly—Lys Peptide (SEQ ID NO:2) 2:
      Leu—Val—Gln—Ala—Phe—Gln—Gly—Lys—Val—Asn—Val—Phe—Leu—Gln—Phe Peptide (SEQ ID NO:3) 3:
      Tyr—Leu—Val—Leu—Phe—Phe—Tyr—Pro—Leu—Asp—Phe—Thr—Phe—Val—Cys—Pro—Thr—Glu—Ile—Ile—Xaa—Cys—Pro—Thr—Glu—Ile—Ile—Gly Computer searches with sequences in the EMBL database indicate that the first two peptides share no significant homology with any known sequences. In contrast, the first 19 residues of the third peptide are identical to residues 95-113 of a deduced sequence from a murine erythroleukemia related gene MER5 (12).

IDENTIFICATION OF NKEF FROM K562 CELLS

Since NK sensitive K562 tumor cells are of erythroid lineage, the existence of NKEF in K562 cytosol was verified. To prepare K562 cytosol, the K562 cells were washed three times with Dulbecco's phosphate buffered saline (PBS). The cells were then resuspended in PBS at $2 \times 10^7$ cells/ml. After 3 cycles of freezing and thawing, the cell lysate was microfuged at 10,000 rpm for 2 minutes and the cytosol was harvested for testing. RBC cytosol and K562 cytosol (10 μl/well) at a number of different protein concentrations were added into ELISA plates, incubated for 1 hr. at 37° C., and washed with phosphate buffered saline (pH 7.2). The plates were coated with 100 μl of 2% fetal bovine serum in PBS for another 1 hr. and washed. Rabbit sera (1/100 dilution, 100 μl/well) were added and incubated for 1 hr. After washing, goat anti-rabbit Ig-conjugated with alkaline phosphatase (Sigma, St. Louis, Mo.) (1/1000 dilution, 100 μl/well) was added. Color was developed by adding p-nitrophenyl phosphate 2 mg/ml in diethanolamine buffer, pH 9.8, 200 μl/well) after washing with PBS and 0.2% Triton X-100. Optical density was measured at 405 nm.

The ELISA tests show that rabbit anti-NKEF antibody also reacts with K562 cytosol.

Samples containing NKEF from both RBC and K562 cytosol were treated with 2.5% 2-mercaptoethanol and separated by SDS-PAGE (11) with a 12% slab gel. Immediately following separation by SDS-PAGE the gel was treated with transfer buffer and blotted onto a nitrocellulose paper (11). After blocking with 5% human serum albumin in blocking buffer, the nitrocellulose paper was incubated with 1/1000 dilution of rabbit anti-human NKEF serum for 16 hr. at room temperature. The nitrocellulose paper was washed, and treated with 1/500 dilution of goat anti-rabbit Ig conjugated with alkaline phosphatase for 2 hr. at room temperature. After washing the color was developed by adding BCIP/NBT substrate (Bethesda Research Laboratories, Gaithersburg, Md.). The molecular masses of the bands were determined from the prestained standards (Bio-Rad, Richmond, Calif.) in parallel lanes. Western blot analysis confirmed that the KNEF from K562 cytosol has the same 24,000 daltons molecular weight as that from RBC. A faint band was also sometimes detected at 48,000 daltons by Western blot analysis in the K562 cytosol and RBC cytosol.

In addition, cytospin slides of K562 were fixed with acetone for 1 hr., then treated with 2% NP-40 for 30 min. The slides were sequentially washed and treated with rabbit anti-NKEF serum and alkaline phosphatase conjugated goat anti-rabbit Ig. The color was developed by adding BCIP/NBT substrate. Immunohistological staining of K562 with anti-NKEF serum shows that this factor is present in K562 cytosol.

The test used to measure NK activity was the standard 4 hour chromium release using K562 erythroleukemic cells as target cells (8). The K562 erythroleukemic cell line was maintained in 10% fetal bovine serum and RPMI1640 medium supplemented with antibiotics. 5000 [$^{51}$Cr] labeled K562 cells were added with peripheral blood lymphocytes (PBL) in round bottom microwells and centrifuged for 4 minutes at $50 \times g$ to initiate cytotoxicity. Total volume of culture medium in each well was 200 μl. After a 4 hour incubation at 37° C., 100 μl of supernate was collected from each well for measuring radioactivity released from killed K562 cells. The effector cell:target ratio used was 40:1 unless indicated otherwise below. Percent cytolysis was calculated as [(Observed cpm—spontaneous cpm)/(Maximal cpm—spontaneous cpm)]×100%. Each assay was done in triplicate and the results are presented as % cytotoxicity ±S.E.M.

To test for NKEF activity, different samples were added into microwells (100 μl/well) before the NK assay and incubated at 37° C. for 1 hour. The microwells were washed 3 times with PBS and then incubated for another 1 hr. at 37° C. with 100 μl of culture medium. After removal of the culture media, PBL and K562 were added to the microwells to initiate the NK assay. NKEF activity was indicated by an increase of NK cytolysis over control that is significant at the 0.05 level.

RBC cell lysates containing NKEF, when coated on the plastic surface of microtiter wells, enhance NK cytotoxicity. To verify that NKEF enhances NK activity, the RBC cytosol and membrane were separately coated on the surface of microtiter wells and tested for effects on cytotoxicity. It was found that NK activity is significantly increased in the microwells pre-coated with RBC cytosol. The increase was observed in all three effector cell:target cell ratios tested as compared with control wells. In contrast, NK activity in wells coated with RBC membrane showed no increase over controls. No difference in NK activity was observed between untreated wells, wells coated with PBS, and wells coated with 10% human AB serum (data not shown).

While RBC cytosol-coated wells enhance NK activity, addition of RBC cellular components directly into chromium release assays had no effect on NK cytotoxicity. Neither RBC cytosol or membrane, nor the combination of these two components, significantly influenced NK activity when added into the assay. Where RBC membrane and cytosol were compared, the microwells were pretreated with 0.5% glutaraldehyde for 30 min. at 37° C. before coating with the membrane preparations in order to anchor RBC membrane on the plastic. The glutaraldehyde treatment had neither a direct effect on NK activity nor did it influence regulation of NK by RBC cytosol or membrane. These results show that NKEF is a water soluble protein located in the RBC cytosol, but not the RBC membrane. These results also demonstrate that NK cell activity is enhanced when NKEF is linked to an anchor molecule.

ENHANCEMENT OF IL-2 INDUCTION OF LAK CELLS

NKEF also enhances interleukin-2 (IL-2) induction of lymphokine activated killer (LAK) cell function and proliferation. NKEF partially purified from RBC cytosol by 50% saturated ammonium sulfate and Q-Sepharose ion exchange chromatography was coated on the surface of tissue culture wells and washed as described above. PBL ($10^6$ cell/ml) were cultured at 37° C. in the tissue culture wells in the presence of recombinant human IL-2 analog (ser 125) (Amgen, Inc., Thousand Oaks, Calif.) for 4 days. The lymphocytes were then collected and tested for cytotoxicity in a 4 hr. chromium release assay using the melanoma UCLA-SO-M14 (M14) cell line as target cells with 4 different effector cell:target cell ratios ranging from 20:1 to 2.5:1. The results showed that NKEF pre-coated on the plastic greatly enhances IL-2 induction of LAK cytotoxicity both at high (100 u/ml) and low (10 (u/ml) concentrations of IL-2.

NKEF added in solution also significantly enhances LAK induction. Without IL-2, no LAK activity is induced even in the presence of NKEF.

The proliferative response of lymphocytes was measured by incorporation of tritiated thymidine. Lymphocytes collected from 4 day IL-2 cultures were seeded in triplicate in microwells ($10^5$ cells/200 ul/well) and pulsed with 0.5 uCi/well of $^3$H-thymidine (6.7 Ci/mmole) for 4 hr. at 37° C. in a humidified incubator with 5% $CO_2$. The cells were harvested by a PhD harvester (Cambridge Technology, Cambridge, Mass.) and the thymidine incorporated was measured by a scintillation counter.

Similar to LAK induction, IL-2 induced PBL proliferation is also greatly augmented by plastic-anchored NKEF. This enhancement was observed both at high (100 u/ml) and low (10 u/ml) concentrations of IL-2. NKEF in the solution also enhances IL-2 induced PBL proliferation. Without IL-2, NKEF alone does not induce lymphocyte proliferation.

In view of these results, it is believed that NKEF will be effective when combined with IL-2 or other cytokines to induce lymphocyte activation and proliferation. NKEF will be useful for combined immunotherapy with cytokines, such as IL-2, tumor necrosis factor, interferon and the like, to increase the function of B cells, T cells, macrophages, NK cells and other leukocytes.

Having thus described the exemplary embodiments of the present invention, it should be noted by those skilled in the art that the within disclosures are exemplary only and that various alternatives, adaptations and modifications may be made within the scope of the present invention. Accordingly, the present invention is not limited to the specific embodiments as illustrated herein, but is only limited by the following claims.

BIBLIOGRAPHY

1. Trinchieri, G., *Adv. Immunol.*, 47:187-376, 1989.
2. Whiteside, T. L. and Herberman, R. B., *Clin. Immunol. Immunother.*, 53:1-23, 1989.
3. Storkus, W. J. & Dawson, J. R., *Critical Rev. Immunol.* 10:393-416, 1991.
4. Golub, S. H., D'Amore, P. and Rainey, M., "Systemic Administration of Human Leukocyte Interferon to Melanoma Patients. II. Cellular Events Associated With Changes in NK Cytotoxicity," *J. Nat'l. Cancer Inst.* 68:711-717, 1982.
5. Ebina, N., Gallardo, D., Shau, H., and Golub, S. H., *Br. J. Cancer*, 62:619-623.
6. Swisher, S. G., Economou, J. S., Holmes, E. C., and Golub, S. H., *Cell Immunol.*, 128:450-461, 1991.
7. Iho, S., Shau, H., and Golub, S. H. *Cell. Immunol.*, 135:66-67.
8. Shau, H. and Golub, S. H., Cell. Immunol., 116:60-72, 1989.
9. Plunkett, M. L., Sanders, M. E., Slevaraj, P., Dustin, M. L., and Springer, T. A. *J. Exp. Med.*, 165:664-676, 1987.
10. Perussia, B., Starr, S., Abraham, S., Fanning, V., and Trinchieri, G., *J. Immunol.*, 130:2133-2141, 1983.
11. Euhus, D. M., Gupta, R. K., and Morton, D. L., *Cancer Immunol. Immunother.* 32:214-220, 1990.
12. Yamamoto, T., Matsui, S., Natori, S., and Obinata, M. *Gene* 80:337-343, 1989.
13. Pross, H. F., Baines, M. G., Rubin, P., Shrugge, P., and Patterson, M. S. *J. Clin. Immunol.* 1:51-71, 1981.

---

What is claimed is:

1. A purified factor comprising a soluble red blood cell cytosol protein having a molecular mass of between 300 and 400 kilodaltons and an apparent molecular weight of about 48 kilodaltons as determined by non-reducing sodium dodecylsulfate polyacrylamide gel electrophoresis.

2. A purified factor according to claim 1 wherein said red blood cell cytosol protein includes the peptide sequence set forth in Seq. I.D. No. 1.

3. A purified factor according to claim 1 wherein said red blood cell cytosol protein includes the peptide sequence set forth in Seq. I.D. No. 2.

4. A purified factor according to claim 1 wherein said red blood cell cytosol protein includes the peptide sequence set forth in Seq. I.D. No. 3.

5. A purified factor according to claim 2 wherein said red blood cell cytosol protein includes the peptide sequence set forth in Seq. I.D. No. 2.

6. A purified factor according to claim 5 wherein said red blood cell cytosol protein includes the peptide sequence set forth in Seq. I.D. No. 3.

7. A composition of matter for use in enhancing the activity of natural killer cells, said composition comprising an anchor moiety to which is linked a soluble red blood cell cytosol protein having a molecular mass of between about 300 and 400 kilodaltons and an apparent molecular weight of about 48 kilodaltons as determined by non-reducing sodium dodecylsulfate polyacrylamide gel electrophoresis.

8. A composition of matter for use in enhancing the activity of natural killer cells according to claim 7 wherein said red blood cell cytosol protein includes the peptide sequence set forth in Seq. I.D. No. 1.

9. A composition of matter for use in enhancing the activity of natural killer cells according to claim 7 wherein said red blood cell cytosol protein includes the peptide sequence set forth in SEQ. ID NO.: 2.

10. A composition of matter for use in enhancing the activity of natural killer cells according to claim 7 wherein said red blood cell cytosol protein includes the peptide sequence set forth in SEQ. ID NO.: 3.

11. A composition of matter for use in enhancing the activity of natural killer cells according to claim 8 wherein said red blood cell cytosol protein includes the peptide sequence set forth in SEQ. ID NO.: 2.

12. A composition of matter for use in enhancing the activity of natural killer cells according to claim 11 wherein said red blood cell cytosol protein includes the peptide sequence set forth in SEQ. ID NO.: 3.

13. A composition of matter for use in enhancing the activity of natural killer cells according to claim 7 wherein said anchor molecule is a plastic.

14. A method for enhancing the in vivo activity of natural killer cells, said method comprising the step of introducing in vivo a soluble red blood cell cytosol protein having a molecular mass of between 300 and 400 kilodaltons and an apparent molecular weight of about 48 kilodaltons as determined by non-reducing sodium dodecyl sulfate polyacrylamide gel electrophoresis wherein said red blood cell cytosol protein is linked to an anchor moiety and wherein the amount of said cytosol protein linked to said anchor moiety is sufficient to enhance the activity of said natural killer cells in vivo.

15. A method for enhancing the in vivo activity of natural killer cells according to claim 14 wherein said red blood cell cytosol protein includes the peptide sequence set forth in Seq. I.D. No. 1.

16. A method for enhancing the in vivo activity of natural killer cells according to claim 14 wherein said red blood cell cytosol protein includes the peptide sequence set forth in SEQ. ID NO.: 2.

17. A method for enhancing the in vivo activity of natural killer cells according to claim 14 wherein said red blood cell cytosol protein includes the peptide sequence set forth in SEQ. ID NO.: 3.

18. A method for enhancing the in vivo activity of natural killer cells according to claim 15 wherein said red blood cell cytosol protein includes the peptide sequence set forth in SEQ. ID NO.: 2.

19. A method for enhancing the in vivo activity of natural killer cells according to claim 18 wherein said red blood cell cytosol protein includes the peptide sequence set forth in SEQ. ID NO. 3.

20. In a method for inducing leukocyte activation and proliferation wherein said leukocytes are treated with IL-2, the improvement comprising treating said leukocytes with said IL-2 in the presence of a sufficient amount of the factor identified in claim 1 to increase the activation and proliferation of said leukocytes.

* * * * *

UNITED STATES PATENT AND TRADEMARK OFFICE
CERTIFICATE OF CORRECTION

PATENT NO. : 5,250,295
DATED : October 5, 1993
INVENTOR(S) : Shau et al.

It is certified that error appears in the above-indentified patent and that said Letters Patent is hereby corrected as shown below:

In column 1, line 5, please change "3442" to --34442--.

Signed and Sealed this

Eleventh Day of October, 1994

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
        ( A ) LENGTH: 20 amino acids
        ( B ) TYPE: amino acid
        ( C ) TOPOLOGY: linear ( i i ) MOLECULE TYPE: protein and peptide ( i x ) FEATURE:
        ( A ) NAME/KEY:
        ( B ) LOCATION:
        ( C ) IDENTIFICATION METHOD: HPLC C18
            column; Proton 1090E Sequencer
        ( D ) OTHER INFORMATION: Peptide is found in
            protein present in red blood cell cytosol ( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:

( x i ) SEQUENCE DESCRIPTION: SEQ ID NO: 1:

```
Gly  Leu  Phe  Ile  Ile  Asp  Tyr  Thr  Asp  Glu
                    5                          10

Met  Gly  Glu  Val  Xaa  Pro  Ala  Gly  Gly  Lys
                    15                         20
```

( 2 ) INFORMATION FOR SEQ ID NO: 2:

( i ) SEQUENCE CHARACTERISTICS:
        ( A ) LENGTH: 15 amino acids
        ( B ) TYPE: amino acid
        ( C ) TOPOLOGY: linear ( i i ) MOLECULE TYPE: protein and peptide ( i x ) FEATURE:
        ( A ) NAME/KEY:
        ( B ) LOCATION:
        ( C ) IDENTIFICATION METHOD: HPLC C18
            column; Proton 1090E Sequencer
        ( D ) OTHER INFORMATION: Peptide is found in
            protein present in red blood cell cytosol ( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:

( x i ) SEQUENCE DESCRIPTION: SEQ ID NO: 2:

```
Leu  Val  Gln  Ala  Phe  Gln  Gly  Lys  Val  Asn
                    5                          10

Val  Phe  Leu  Gln  Phe
                    15
```

( 2 ) INFORMATION FOR SEQ ID NO: 3:

( i ) SEQUENCE CHARACTERISTICS:
        ( A ) LENGTH: 28
        ( B ) TYPE: amino acid
        ( D ) TOPOLOGY: linear ( i i ) MOLECULE TYPE: protein and peptide ( i x ) FEATURE:
        ( A ) NAME/KEY:
        ( B ) LOCATION:

```
    (C) IDENTIFICATION METHOD: HPLC C18
        column; Proton 1090E Sequencer
    (D) OTHER INFORMATION: Peptide is found in
        protein present in red blood cell cytosol.

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:

(xi) SEQUENCE DESCRIPTION: SEQ ID NO: 3:

Tyr Leu Val Leu Phe Phe Tyr Pro Leu Asp
                 5                   10

Phe Thr Phe Val Cys Pro Thr Glu Ile Ile
                 15                  20

Xaa Cys Pro Thr Glu Ile Ile Gly
                 25
```